US011016000B2

(12) United States Patent
    Alghamdi (10) Patent No.: US 11,016,000 B2
(45) Date of Patent: May 25, 2021

(54) PURGING FOR WELDING

(71) Applicant: Saudi Arabian Oil Company, Dhahran (SA)

(72) Inventor: Tariq Abdulwahed Ali Alghamdi, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 412 days.

(21) Appl. No.: 16/059,901

(22) Filed: Aug. 9, 2018

(65) Prior Publication Data

US 2020/0049584 A1   Feb. 13, 2020

(51) Int. Cl.
    *G01M 3/28*    (2006.01)
    *G01N 33/00*   (2006.01)
    *B23K 9/32*    (2006.01)
    *B23K 101/10*  (2006.01)

(52) U.S. Cl.
    CPC ........ *G01M 3/2807* (2013.01); *G01M 3/2884* (2013.01); *G01N 33/0016* (2013.01); *B23K 9/326* (2013.01); *B23K 2101/10* (2018.08)

(58) Field of Classification Search
    CPC .............. G01M 3/2807; G01M 3/2884; G01N 33/0016; B23K 9/326; B23K 9/095; B23K 9/16; B23K 9/0282; B23K 2101/10; B23K 2101/06; B23K 35/383
    See application file for complete search history.

(56) References Cited

U.S. PATENT DOCUMENTS

| 4,341,237 A | 7/1982 | Stauffer |
| 4,916,281 A | 4/1990 | Flasche et al. |
| 6,610,957 B2 | 8/2003 | Uttrachi |
| 2007/0199593 A1* | 8/2007 | Mends ............... F16L 25/02 137/1 |
| 2016/0221107 A1 | 8/2016 | Kadlec |

OTHER PUBLICATIONS

International Search Report and Written Opinion issued in International Application No. PCT/US2019/045408 dated Oct. 23, 2019, 13 pages.
Sperko, "Purge to Protect Stainless Stell Pipe Welds," Welding Design and Fabrication, May 1995, 2 pages.
Taban et al., "Effect of the Purging Gas on Properties of 304H GTA Welds," Welding Journal, vol. 93, Apr. 2014, 7 pages.
Uttrachi, "MIG Shielding Gas Control and Optimization," available on or before Oct. 14, 2009, [retrieved May 15, 2018], retrieved from URL: <http://netwelding.com/Shielding_Gas_Control_Download.pdf>, 23 pages.
GCC Examination Report issued in GCC Application No. GC 2019-38078 dated Oct. 5, 2020, 4 pages.

* cited by examiner

*Primary Examiner* — Suman K Nath
(74) *Attorney, Agent, or Firm* — Fish & Richardson P.C.

(57) ABSTRACT

A system and method of purge testing for welding piping, including flowing a purge gas through a test pipe, determining concentration of a gas component in the purge gas discharged from the test pipe, and determining a time period to reach a lower threshold of the concentration. The testing may consider different flow rates, pipe sizes, and inlet/outlet bore sizes.

24 Claims, 3 Drawing Sheets

PURGING FOR WELDING

TECHNICAL FIELD

The present techniques relate to welding of alloy materials and the associated purging of the alloy materials.

BACKGROUND

Welding may join metals by fusion. In addition to melting the base metal, a filler material is typically added to the joint to form a weld pool of molten material that cools to form a weld joint. The joint based on the weld configuration can be stronger than the base material or parent metal. The weld configuration may be butt, full penetration, fillet, etc. Energy sources for welding may include a gas flame, an electric arc, a laser, an electron beam, and so on. Welding may rely on a gas shield to protect the filler metals or melted metals from contamination or oxidation. In addition, welding may require backing gas during welding of alloy materials to protect the weld root side and reduce or eliminate oxidation formation.

In the welding of stainless steel materials, the presence of oxygen at the root side can adversely affect the weld. Therefore, the stainless steel materials, such as piping, may be subjected to a purge gas to displace gases inside the pipe and lower the concentration of oxygen adjacent to the weld. For stainless steel piping arranged coaxially to form a weld joint, a purge gas (e.g., argon) may be introduced into the piping. The flowing of the purge gas through the piping can reduce the presence of oxygen or other undesired components in the piping. The purging may be performed before and during the welding.

SUMMARY

An aspect relates to a system for purge testing for welding piping. The system includes a test pipe having a same diameter of the piping to be welded, and a plurality of pipe end closures to fit on an inlet end of the test pipe and on an outlet end of the test pipe, each pipe end enclosure having a bore, wherein the plurality has a range of bore sizes. The system includes an inlet conduit to fluidically couple a gas source to an inlet bore of an inlet pipe-end enclosure disposed on an inlet end of the test pipe, wherein the gas source to discharge purge gas through the inlet conduit and the test pipe. The system includes a flow regulator to control flow rate of the purge gas. Further, the system includes a gas analyzer to measure a concentration of a gas component in the purge gas discharged from the test pipe through an outlet bore of an outlet pipe-end enclosure disposed on an outlet end of the test pipe. In addition, the system has a timing device to measure a cumulative time of the flow of the purge gas through the test pipe.

Another aspect relates to a method of purge testing for welding piping. The method incudes selecting a test pipe from a plurality of test pipes having a range of diameters, wherein the test pipe selected has a same diameter as piping to be welded. The method includes flowing a purge gas at a specified flow rate through the test pipe to decrease presence of a gas component in the test pipe. Further, the method includes determining concentration of the gas component in the purge gas discharged from the test pipe. In addition, the method includes determining a time period of the flowing of the purge gas through the test pipe to reach a lower threshold of the concentration.

Yet another aspect relates to a method of purge-time testing for welding alloy piping. The method includes performing multiple purge-time tests. Test variables include a first variable that is diameter of a test pipe, a second variable that is bore size of pipe end closures installed on each end of the test pipe, and a third variable that is flow rate of a purge gas through the test pipe and the pipe end closures. Performing each test of the multiple purge-time tests further includes measuring concentration of a gas component in the purge gas discharged from the test pipe, and measuring a time period for the concentration to drop to a threshold concentration.

Yet another aspect relates to a method of performing multiple tests to determine purge time for welding piping. The method includes flowing a purge gas at a respective flow rate through a test pipe for each test, the test pipe comprising a same diameter as the piping to be welded. The method includes determining a concentration of a gas component in the purge gas discharged from the test pipe for each test. Further, the method includes determining a respective time period to reach a lower threshold of the concentration for each test. The method also includes specifying a purge time for the welding of the piping correlative with a shortest time period of the respective time periods.

The details of one or more implementations are set forth in the accompanying drawings and the description below. Other features and advantages will be apparent from the description and drawings, and from the claims.

DETAILED DESCRIPTION

An embodiment of the present techniques includes performing a series of purge tests with a test pipe to determine purge time for welding piping. In some examples, the purge time determined may be a pre-welding purge time. The tests typically include flowing a purge gas (e.g., an inert gas) at a respective flow rate through the test pipe for each test. The test pipe will generally have the same diameter as the piping to be welded. In some examples, the test pipe is 1 meter or 2 meters in length, and may be plastic or non-metallic for ease of handling. This exemplary method includes, for each test of the series of tests, determining a concentration of a gas component (e.g., oxygen) in the purge gas discharged from the test pipe. Further, the method includes determining a respective time period to reach a lower threshold of the concentration for each test. Lastly, the method includes specifying a purge time for the welding of the alloy piping correlative with a shortest time period of the respective time periods in the series of tests.

The shortest time period may be for a series of the tests at a given diameter of the test pipe. The shortest time period (shortest purge time) of the tests may be in units of time or time per length. This test shortest time period may be multiplied by the length of the piping to be welded, or by a ratio of the welded piping length to the test pipe length, to give the actual purge time for the welding of the piping.

In some examples to correlate the actual purging time with the shortest time period, the shortest time period may be further multiplied by a factor to give the actual purging time. The factor may be based on an accuracy range, an error margin, placement of the purge-gas inlet and outlet (vent), deviation from steady-state purge-flow conditions in the piping to be welded, an awkward or convoluted configuration of piping to be welded that may inhibit hydraulics, and the like. The factor may be an arbitrary contingency value. In some examples, the factor is dimensionless without units. In certain examples, no factor is applied, or a factor of 1.0 is applied. Lastly, the purge-gas flow rate, vent bore size, and so on, for the test with the shortest time period may also be specified for the actual purging.

In sum, the test purge time to reach the lower threshold or boundary concentration of the undesired gas component may be a basis of the actual pre-welding purge time. In other words, the aforementioned shortest time period may be related to the actual purge time to lower the concentration of the gas component in the piping to be welded. After such purge time is implemented, the piping may be ready for welding. The purge may continue at least through an initial portion of the welding time period but the purge flow rate may be reduced during welding to a rate adequate to maintain the undesired gas-component concentration at or below the lower threshold.

The purge gas may include at least one of argon, nitrogen, hydrogen, or helium. The undesired gas component may be oxygen, nitrogen, air, or other compounds. The aforementioned lower threshold of the concentration of the gas component may be a volume percent of less than 2, 1.5, 1, 0.5, 0.1, 0.05, or 0.02, or a mass percent of less than 2, 1.5, 1, 0.5, 0.1, 0.05, or 0.02. In one example, the lower threshold is a mass basis of 500 parts per million (ppm) oxygen (O2). The test pipe may have a length in a range of 0.5 meter to 10 meters, 1 meter to 6 meters, 1 meter to 3 meters, or 2 meters to 4 meters, and other ranges. The piping to be welded may be an alloy metal piping such as nickel alloy piping or stainless steel piping, and the like.

While the discussion herein may focus at times on purge testing of piping, some embodiments are applicable to purge testing of other alloy components to be welded. Such components may be conduits generally including tubing and other conduits. The components to be purged and welded may also be, for example, mechanical devices, machines, structural components, and process equipment. A representative component may be selected for purge testing. Process equipment may include heat exchangers pumps, vessels, and so forth. For shell-and-tube heat exchangers, the shell side or tube side of a representative heat exchanger may be subjected to purge gas testing. In all, various work pieces or apparatuses may be purged prior to the welding in fabrication or repair, and the welding application benefit from purge testing discussed herein.

In welding alloy materials such as stainless steel components or pipe, mechanical strength and an absence of contamination or oxidation in the root pass are typically targeted. Therefore, purging the volume of the alloy pipe (e.g., stainless steel pipe) prior to and during the welding may be implemented to displace gases, such as oxygen, that react with the molten weld. When welding alloy pipes including stainless steel pipes, the pre-welding purge-gas flow rate and duration may be selected to reduce purging costs and achieve acceptable corrosion performance. The presence of oxygen (and sometimes nitrogen) around the molten weld can lead to wide-ranging defects, metallurgical disparity, discoloration, gross oxidation resulting in significant loss of corrosion resistance, and so forth. Moreover, in certain instances, nitrogen contamination can result in brittleness and cracking during or after cooling of the weld.

In some instances, conducting measurements of oxygen, air, or contaminants during piping construction may be impractical to implement. For example, a gas or oxygen analyzer may not be available in the field or shop during production welding, or conducting oxygen measurements may not be feasible during piping construction, and so on. Thus, the purging time may be calculated based on the purge-gas flow rate and pipe cross-section area, and so forth. The calculation may be made assuming steady state condition for gas expansion and distribution. Therefore, the calculated purge time may not equal or give (or readily correlate with) the actual purging time to prepare the pipe for welding. This calculated determination of purging time may give too short of a purge time or too long of a purge time. A too short purge time may lead to undesirable root oxidation due to ineffective purging. A too long purge time gives over purging which can increase costs and delay project completion.

Embodiments herein improve identification of satisfactory purging conditions of piping for welding. Indeed, the process of gas back-purging for the root section of the weld during open-butt welding of pipe may be improved. The appropriate purging time for welding of different pipe sizes may be determined through testing. The studies may determine a beneficial purging time for each particular pipe size. In examples, such may promote adequate purging coverage and quality weld root, reduce the associated gas purging cost, and expedite project completion schedule. In addition, the purging parameters, e.g., rates of gas flow in back-purging and the vent bleeding-off bore size, can be determined to give acceptable purging time which improves project economics and schedule. The testing analyses may consider or account for formation of turbulence flow inside the welded confined space during purging to determine the appropriate flow rate and purging time prior to start of welding activities.

The test pipe for study can be one solid pipe piece rather than two pipe pieces as used in welding. Indeed, in examples, one piece of pipe can be utilized for the gas-flow time measurement. An oxygen analyzer or sensor may be applied or connected to the purge gas outlet of the test pipe. Purge gas (e.g., argon) is flowed through the test-pipe inlet, test pipe, and test-pipe outlet (purge gas outlet). As the purge gas pushes the air inside the pipe out of the purge gas outlet, the oxygen level sensed by the oxygen sensor decreases. Multiple purge gas flow rates are selected, and at each flow rate, the time taken for the oxygen level to drop below a threshold level is determined. Initially, the time taken for the oxygen level to drop generally decreases with increasing flow rate. However, beyond a particular flow rate, the time taken may increase (see FIG. 5 as an example) because the increasing flow rate causes turbulent flow within the pipes making difficult the flow through the pipes and vent outlet, or because of other reasons.

For the pipe diameters in the experiments or tests, particular flow rates giving the shortest time to reach the lower threshold of oxygen concentration may be selected as the optimal or adequate purge-gas flow rate. The experiments may be repeated for pipes of different diameters and also for various pipe inlet and outlet bore sizes. In some examples, pipe materials specification does not play a significant role in gas purging duration for at least the reason the test pipes may be relatively short in length. Lastly, with the test results, a welding operator may choose the appropriate test flow rate in view of the pipe and vent diameters as a basis for actual purge time and flow rates for the welding.

As for the welding of two pipes together, a purge gas inlet may be formed on one end of the first pipe, and a purge gas outlet formed at the other end of the second pipe. The inlet and the outlet may define bores through which the purge gas flows into and out of the pipes. During purging and welding, the weld joint may be sealed to prevent or reduce leakage of purge gas out of the pipes and leakage (ingress) of air into the pipes. The welding may be initiated contemporaneous with or after the vent of purge gas had reached less than the threshold concentration of the undesired gas component. Then, the purging may be maintained for at least an initial time portion of the welding time period. In one example, the purging is maintained in the welding period for (1) at least three weld passes or (2) 10 millimeter (mm) weld metal thickness. The choice of (1) or (2) as a basis may depend on which is associated with a lower amount of time, or a higher amount of time, or other considerations. In some examples, the purging is aimed to achieve actual oxygen levels inside or exiting the joint (via the vent) no greater than a specified value (e.g., 0.05 vol. %) prior to and during welding, as measured using an oxygen analyzer. In certain instances, the purging during welding may be at a lower flow rate than the pre-welding purging.

Figure 1:
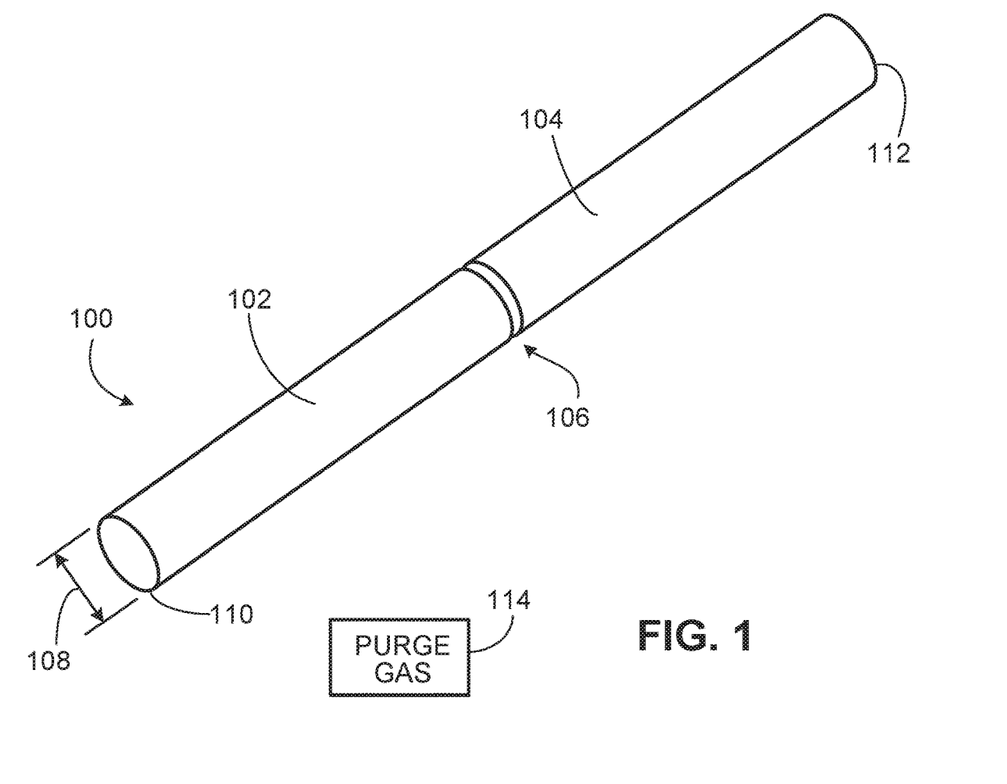
FIG. 1 is a perspective view of piping to be welded.

Turning now to the drawings, FIG. 1 is piping 100 to be welded. Welding may be a joining process that coalesces metals (or nonmetals) by heating the metals to the welding temperature. The welding may include arc welding or stick welding, and/or other welding techniques. For arc welding, the processes may employ a welding power supply to generate and maintain an electric arc between an electrode and the base material to melt metals at the welding point. Direct current (DC) or alternating current (AC), and consumable or non-consumable electrodes, can be used. The welding region is sometimes protected by an inert or semi-inert gas such as a shielding gas. Filler material is sometimes used as well. If arc welding is employed, the arc welding may be gas-shielded metal arc welding (SMAW), metal inert gas (MIG) welding or gas metal arc welding (GMAW), tungsten inert gas (TIG) welding or gas tungsten arc welding (GTAW), flux-cored arc welding (FCAW), plasma arc welding (with tungsten electrode), and so forth.

Gas tungsten arc welding may employ a shielding gas (e.g., Argon or Ar) in root and hot pass welding of stainless steel pipe. Such TIG welding may be applicable for weldable metals generally and, in particular, for stainless steel and light metals. The GTAW or TIG welding may be a manual welding process that uses a non-consumable tungsten electrode, an inert or semi-inert gas mixture (an externally supplied gas for shielding), and a separate filler material.

The piping 100 may be alloy piping such as nickel alloy piping, stainless steel piping, corrosion-resistant alloy piping, or other types or blends of alloy piping. Nickel alloy piping may include nickel copper alloys, nickel chrome base alloys, and so on. Stainless steel is generally a steel alloy with at least 10.5 weight % chromium. Stainless steels can provide corrosion resistance which generally increases with increasing chromium content. Additions of molybdenum may increase corrosion resistance. Stainless steel designations include at least a 200 series, 300 series, and 400 series. Common types of stainless steel include Type 304 (or SS304) and Type 316 (or SS316), and the like. A letter designation can be added to denote a specific variation in the steel alloy composition including with respect to the carbon contribution.

As indicated, oxygen (O2) contamination in stainless steel welding can adversely affect the weld such as in forming an oxide layer on the root surface of the weld bead. As also indicated, weld root quality of stainless steel pipe and tubes can be promoted by removing the air from the fusion zone or weld zone with a purge gas such as an inert purge gas.

In FIG. 1, the piping 100 includes a first pipe 102 and a second pipe 104 placed in position to be welded together, as indicated by arrow 106. In examples, the first pipe 102 and second pipe 104 may be arranged coaxially to form a weld joint. Further, in the illustrated embodiment, the first pipe 102 and the second pipe 104 each have the same nominal diameter 108. As for welding, the two coaxial pipes 102 and 104 in weld fabrication may have an open joint groove to be welded. In certain examples, this groove may be taped to prevent or reduce air ingress into the pipe and prevent or reduce leaking of purging gas from the piping.

In general, the first weld pass in the welding of two members to form one structure may be labeled as the root pass. The root pass may be the first run weld metal deposited on an open joint or the bottom of the groove being welded between the first pipe 102 and the second pipe 104. Subsequent passes may increase the weld depth to the desired thickness, yielding the desired strength.

Purging to protect the root side of alloy pipe weldments can be relatively expensive and time consuming. Yet, as discussed, the fabricator in welding the piping may benefit by preventing or reducing oxygen contamination of the weld root or root pass. A purge gas source 114 can provide purge gas (e.g., argon) to the piping 100 to lower concentration of a gas component, such as oxygen or air, in the piping prior to and during the welding. In some examples, the purge gas may be labeled as "backing gas," and the purging labeled as "back purging."

Opposite the welding, the end 110 of the first pipe 102 and the end 112 of the second pipe 104 are open pipe or open-ended pipe in the illustrated example. The ends 110 and 112 may be temporarily configured with, for instance, pipe end closures to receive or discharge a purge gas. For piping 100 with more than one outlet end 112, more two pipe end closures may be employed. In the illustrated example, two pipe end closures (not shown) each having a bore may be placed on the ends 110 and 112, respectively. One of the installed pipe-end closures may be an inlet to receive the purge gas, and the other installed pipe-end closure will discharge or vent the purge gas.

As discussed for instances where a gas or oxygen analyzer is not available or not feasible to employ, the purge (backing) gas flow rate and time may be calculated to give a theoretical volume change and purging time for the enclosed pipe volume. Moreover, extra purging time is sometimes employed if the purge gas inlet and outlet (vent) cannot be placed at opposite ends of the enclosed volume in order to promote complete or near-complete displacement of the original air. As mentioned, purging may be implemented before the welding and also during the welding. In a particular example, the purging process is aimed to achieve actual oxygen levels inside or exiting the joint (via the vent) no greater than 0.05 vol. % prior to and during welding, as measured using an oxygen analyzer. At the initiation of the welding, the purging may be maintained for at least a specified number of welding passes or until a specified value (e.g., 10 mm) of weld metal thickness is reached.

The purging time (pre-weld) for pipe sizes may be calculated with the following equation: $Q=v \times (\pi D^2)/4$, wherein Q is the flow rate of the purging gas in unit volume per time, v is the unit area speed for purge gas flow or velocity in units of length per time, and D is the internal diameter of carrier pipe (piping being welded). The formula $(\pi D^2)/4$ may represent the cross section area of the pipe opening. The bore section area in measured in unit of length squared. From the above equation for Q, the flow velocity of the gas can be calculated taking to consideration that flow rate of the gas and pipe bore cross section area are given. From the calculated velocity, the purge time can be further calculated because the test pipe length is typically known. The actual time of purging appropriate in the field may be higher than this calculated purging time determined via the above equation. This variation, in some instances, can be attributed to the assumption of steady state for gas expansion in use of the above equation.

Testing determination of an adequate actual purging time for respective pipe sizes as disclosed herein can identify adequate purge-gas flow rates for each relevant pipe size. The determination may generally involve a test or series a tests. Use of flow or hydraulic equations, such as the above equation, or other equations, may be employed along with the tests in some determinations. Lastly, for some examples, more flow rate of the inert purge gas may not always decrease oxygen content because the higher flow rates may increase turbulence which can inhibit displacing the oxygen out of the mixed gas. The mixed gas may be the purge gas and initially resident air.

Again, the purging can be implemented for stainless steel and low-alloy materials before and during welding to prevent or reduce weld root oxidation. This application may be for alloyed materials piping in various new construction projects and existing operating facilities. The back purge for low-alloy steel may be specified to reduce the oxygen level below a certain concentration (e.g., 1 vol. %) in the enclosed volume. The back purge for stainless steel and nickel alloys may be specified to reduce the oxygen level to below an even lower concentration (e.g., 0.05 vol. %).

An oxygen analyzer, such as a handheld analyzer, installed sensor, etc., can measure or facilitate determination of the oxygen content inside the pipe during purging. However, if the analyzer is unavailable, or oxygen measurements are not practical during piping construction, the purging time may be calculated based on the purge-gas flow rate and pipe-bore cross section area. As discussed, this calculation of time in some instances may be made assuming steady state condition for gas expansion and distribution. Accordingly, such a calculated time may not equal the actual purging time to adequately lower the oxygen concentration in the piping for welding, or may exceed the adequate or appropriate actual purging time resulting in wasted purge gas and possibly project delay. In response, embodiments of testing herein determine an appropriate, adequate, or optimum gas purging time for different pipe sizes based on different vent hole sizes, including with respect to adequate flow rate versus purging time.

Figure 2:
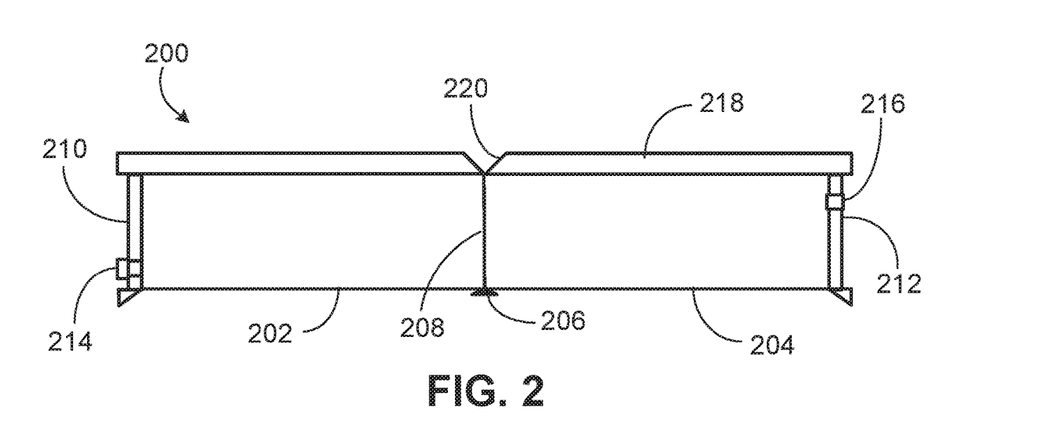
FIG. 2 is a diagram of piping being welded.

FIG. 2 is piping 200 including a first pipe 202 being welded to a second pipe 204. Welding may be a joining process of metals by heating the metals to the welding temperature, with or without the application of pressure, or by pressure alone, and with or without the use of filler metals. As mentioned, welding may include shielded metal arc welding, gas metal arc welding, gas tungsten arc welding, and the like. Shielding gas may be an externally supplied gas or gas mixture. As also discussed, gas tungsten arc welding (GTAW) or TIG welding may coalesce metals by heating the metals with an arc between a tungsten electrode and the work piece. In the example of FIG. 2, the work piece is the piping 200 being welded. The welding electrode may be a component of the welding circuity that terminates at the arc, and in some instances, may also be a source of filler material.

Welds can be geometrically prepared in different ways. Example types of weld joints include butt joint, edge joint, lap joint, corner joint, T-joint, and so forth. Double-V preparation joints may be characterized by the two pieces of material each tapering to a single center point at about one-half their height. Single-U and double-U preparation joints have straight edges similar to the single-V and double-V preparation joints but are curved forming the shape of a U. Moreover, differing lap-joint geometries may be employed. In all, a variety of weld geometries may implemented to weld two metal components together.

The base metal or the metal to be welded, such as the piping 200 or the first pipe 202 and second pipe 204, may be referred to as the "work piece." The weld metal may be the portion of the base metal melted during welding. The heat-affected zone (HAZ) may be the portion of the base metal not melted but affected by the heat of welding. The HAZ may be a ring surrounding the weld. The temperature of the welding process, combined with the stresses of uneven heating and cooling, alter the heat-treatment properties of the alloy in the HAZ.

A weld pass may be a single progression of welding along the joint. The result of a pass may be a weld bead. The stringer or root bead may be the first pass in the weld, typically without significant weaving motion. In some examples, the hot pass may be the weld pass that immediately follows the root pass. The filler passes may follow the hot pass and fill the weld groove flush or nearly flush with the surface of the work pieces. A cover pass may be the weld pass that finishes or completes the welded joint. The cover bead may be higher than or elevated above the adjacent surface and overlaps the groove.

In the welding in this example, a weld joint 206 is formed at an interface 208 of the first pipe 202 and the second pipe 204. In general, a weld joint may be the junction of members or the edge of members to be joined. The joint may be beveled or otherwise designed or configured for welding. As discussed, the joint may have, for example, a V groove or U groove. The joint may be a butt weld, fillet weld, and so on. In the illustrated embodiment, the joint 206 may be formed from a groove 220 of the wall 218 of the pipes 202, 204. Prior to welding for purging of the piping, the groove or joint may be sealed with tape such as masking tape.

A pipe end closure 210 is installed on an end of the first pipe 202 and another pipe end closure 212 is installed on an end of the second pipe 204. A pipe end closure is aimed to block a pipe either side of the weld zone so that the air can be purged out of the space between them and around the weld root. These closures 210, 212 can be an inflatable device or system, a mechanical disc or plug assembly, and the like. The material of closures 210, 212 is generally not porous material and do not readily absorb oxygen and water vapor, such as polystyrene, as such may prevent an oxygen-free environment in the pipe 202, 204 from being achieved. In the illustrated example, the pipe end closure 210 on the first pipe 202 has a bore 214 that is an inlet for purge gas. The pipe end closure 212 on the second pipe 204 has a bore 216 that is an outlet (vent) for the purge gas. The depicted rectangle at the inlet 214 is merely to indicate inlet tubing connected to the bore 214. The pipe end closures 210, 212 may be the same. The depicted triangle at the bottom of each pipe end enclosure 210, 212 is merely to indicate for clarity that the cross-section wall thickness of the pipe is not depicted at the bottom side of the pipes 202, 204. The bores 214, 216 may be the same size. The bores 214, 216 may be holes and may include fittings such as nipples to couple to piping or tubing.

After welding, regions in the weld area include the fusion zone which may be the weld itself where the filler metal was laid during the welding process. The properties of the fusion zone may depend on the filler metal including the compatibility of the filler material with the base materials. As mentioned, a heat-affected zone (HAZ) may generally surround the fusion zone and which is an area not melted but with microstructure and properties altered by the weld. The HAZ properties may depend on behavior of the base material when subjected to heat. The metal in the HAZ area can be weaker than the base material and the fusion zone, and is also where residual stresses may be found.

With welding as an industrial or construction process, the cost of welding may play a role in manufacturing decisions. Different variables including equipment cost, labor cost, material cost, and energy cost affect the cost of welding. The equipment cost for shielded metal arc welding may be relatively inexpensive compared to other welding techniques such as laser beam welding and electron beam welding. Moreover, energy costs typically do not amount to more than a few percent of the total welding cost, and may depend on arc time, welding power demand, and other factors.

The cost of materials may include the cost of the base and filler material, and the cost of shielding gases and purge gases, and so on. In general, labor cost may depend on preparation of the work piece, the deposition rate (the rate of welding), the hourly wage, and the total operation time. The operation time may include time spent purging, fitting, welding, and handling the part. For manual welding methods, labor costs may make up a bulk of the total cost of welding. Consequently, cost-saving measures may focus on reducing operation time of preparing for and performing the weld.

Embodiments herein provide for purge time and flow-rate adequate for oxygen displacement but without unduly excessive purge time or purge gas consumption. Thus, costs may be reduced and project schedule advanced. An overall project may include the fabrication and installation of the piping as a component of the project, and overall project schedule met or improved with reduction in purge time of the welding.

As for purging the piping (e.g., piping 100, piping 200, or other piping) prior to welding, experiment analyses via a testing system and method may be carried out to determine recommended gas-purge flow rate and adequate outlet bore size at which a low purging time can be achieved for different pipe sizes. Different purging flow rates and outlet hole sizes can generally be applied for each pipe size (diameter). An oxygen analyzer may monitor the oxygen concentration in the volume of the test pipe or spool. The experiment or test may be turned off or switched off each time the volume oxygen content drops to a lower threshold (e.g., 0.05 vol. % or less), and the associated purging time recorded.

During testing, as the flow rate is increased for each particular pipe size and vent diameter, the purging time until O2 concentration drops to 0.05% will generally be reduced. However, at a certain flow rate in the ramp-up of low rate, the purge time may potentially increase. As discussed, this may be due to more turbulent flow and mixing of piping gases with backing gas at the higher purge-gas flow rates. This makes the displacement and removal of oxygen more challenging. The change in the time-flow rate curve may lead to the adequate flow rate and low purging time for a specific pipe size and vent hole diameter.

The experiments or tests may be conducted for different sizes and conditions. See, for example, FIG. 4. To calculate the anticipated purging time for longer pipe (e.g., the pipe in the field or shop to be welded), the test purging time obtained from this study with the test pipe (e.g., 1 meter pipe long) can be multiplied by the actual pipe length (of the longer pipe to be welded). In particular, the test purging time may be multiplied by the actual pipe length and divided by the test pipe length. Thus, the test purging time (e.g., per length of test pipe) may be multiplied by a ratio of field pipe length over test pipe length. Additional factors or ratios may be considered. Moreover, prior to evaluating the anticipated time of actual purging time for the pipe to be welded, the testing may be validated by purging with a longer test pipe, e.g., 3 meters in length, versus the first test pipe, e.g., having a length of 1 meter.

Figure 3:
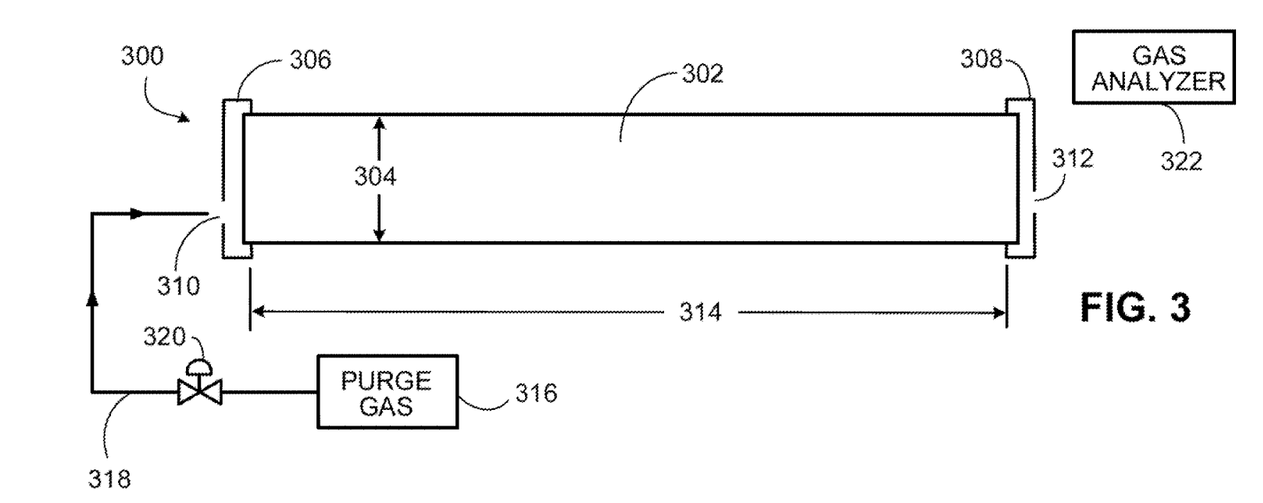
FIG. 3 is a diagram of a testing arrangement for purge testing for welding piping.

FIG. 3 is a testing system or testing arrangement 300 including a test pipe 302 for conducting purge-time testing for welding piping. The test pipe 302 typically has a nominal diameter 304 that is the same as the nominal diameter of the piping to be welded. Multiple test pipes 302 having different nominal diameters 304 may be employed in multiple respective tests of the purge time for the welding piping of various nominal diameters. The test pipe 302 may be a straight piece of pipe and at each end may be fully open (pipe nominal diameter). The test pipe 302 may also be labeled a pipe piece or test spool, and the like.

The testing arrangement 300 may include pipe end closures 306 and 308 disposed or installed on ends of the test pipe 302. Practically, if argon gas or similar gas is used for purging, the inlet gas bore may be made at bottom side of one pipe assembly end, and the outlet bore may be made at top side of the other end. This confirmation is recommended based on the fact that argon gas weight is higher than the weight of air. In this case, the argon gas will accumulate at bottom and discharge from the pipe from the topside. If the gas monitor shows little or no oxygen in the outlet section, such may generally confirms that little or no oxygen exists inside the pipe. For testing purpose, the inlet and outlet bore may be installed in the centers of the closure ends which may be more conservative. In the illustrated embodiment, the pipe end closure 306 has a bore 310 that is an inlet to receive purge gas into the test pipe 302. The other pipe end closure 308 has a bore 312 that discharges or vents purge gas from the test pipe 302. In examples, the bore size of the inlet pipe end closure may be the same as the vent bore size of the outlet pipe end closure. Moreover, a group of multiple pipe end closures 306 and 308 having a range of various bore 310, 312 sizes may be employed for respective purge-time tests. In other words, a particular size of bore 310, 312 of a pipe end closure 306 and 308 may be selected as a variable in the testing. A group of pipe end closures 308 having differing bore 312 sizes can be utilized to provide different vent sizes for the purge gas for multiple tests.

The length 314 of the test pipe 302 may 1 meter, 2 meters, 3 meters, 4 meters, 5 meters, 6 meters, 7 meters, 8 meters, 9 meters, or 10 meters, or values there between. A long length 314 (e.g., greater than 10 meters) is typically not needed for the testing. In some embodiments, the length 314 is in a range of 0.5 meter to 2.5 meter for convenience or ease of handling. In one example, the length 314 is about 1 meter or 2 meters. Test pipes 302 having longer lengths 314 may be selected for a subsequent test to validate a previous test that employed a test pipe 302 having a shorter length. In some examples, test pipes 302 used for validation have a length 314 in a range of 3 meters to 10 meters.

As discussed, to determine the actual purge time (pre-welding purge time), the test pipe 302 purge time may be multiplied by a ratio of the welded pipe length to the test pipe 302 length. For example, if the purge time with a test pipe 1 meter in length is 2 minutes, and the piping to be welded is 25 meters in length, then the pre-welding purge time in the field for the piping to be welded may be at least 50 minutes or correlated with 50 minutes. Such may assume steady state conditions in the field. Additional factors may be applied to the 50 minutes to determine the pre-welding purge time for the piping to be welded.

The material of the test pipe 302 may be non-metallic, plastic, or metal. Non-metallic test pipes 302 may be lighter and less expensive than metal or steel test pipes 302. Examples of non-metallic materials for the pipes 302 may be reinforced thermosetting resin (RTR), high density polyethylene (HDPE), and so on. The material of the pipe 302 may not significantly impact the study due to the relatively short lengths 314 of the test pipe 302. In other words, the difference in effects of pipe materials and friction factors of various test pipe 302 materials on purge gas flow may be negligible for short test pipes 302. However, some examples may account for the different friction factors of non-metallic test pipes 302 versus metallic test pipes 302, and versus the alloy or stainless steel piping to be welded, and so on.

A purge gas source 316, such as a gas cylinder or pipe supply header, may provide purge gas to the test pipe 302. For instance, the purge gas source 316 may discharge purge gas through a supply or inlet conduit 318 to the inlet bore 310 of the pipe end closure 306 and through the test pipe 302. A control valve 320, such as a flow regulator included with the gas cylinder, may regulate the flow rate of the purge gas. Such a regulator may also indicate the flow rate such as with a gauge. A purging gas cylinder may be equipment with a calibrated flow gas regulator system displaying the actual flow rate. The set point of the control valve or regulator 320 for the flow rate of the purge gas may be changed or adjusted.

In operation, the purge gas may exit the test pipe 302 through the vent or outlet bore 312 of the pipe end closure 308. A gas analyzer 322, such as a handheld gas analyzer 302, may measure a concentration of a gas component in the purge gas discharged from the test pipe 302. This concentration (e.g., oxygen content) may be typically measured intermittently but can be measured continuously or substantially continuously in some examples. The purge gas may be argon, nitrogen, hydrogen, or helium, or any combinations thereof. In come embodiments, the gas analyzer 322 is an oxygen (O2) analyzer, and the gas component measured via the gas analyzer 322 in the discharged purge gas is oxygen.

One embodiment of the present techniques is a method of purge testing for welding piping, including installing pipe end closures having respective bore sizes on each end of a test pipe for respective tests, the test pipe having a same diameter as the piping to be welded. The method includes flowing a purge gas at respective specified flow rates through the test pipe and pipe end closures for respective tests. Further, the method includes determining a concentration of a gas component in the purge gas discharged from the test pipe for each test. The method determines respective time periods to reach a lower threshold of the concentration for the tests. In addition, the method includes identifying a purge time for the welding of the piping correlative with a shortest time period of the respective time periods. Lastly, the method includes purging the actual piping for at least the purge time specified and welding the piping.

Figure 4:
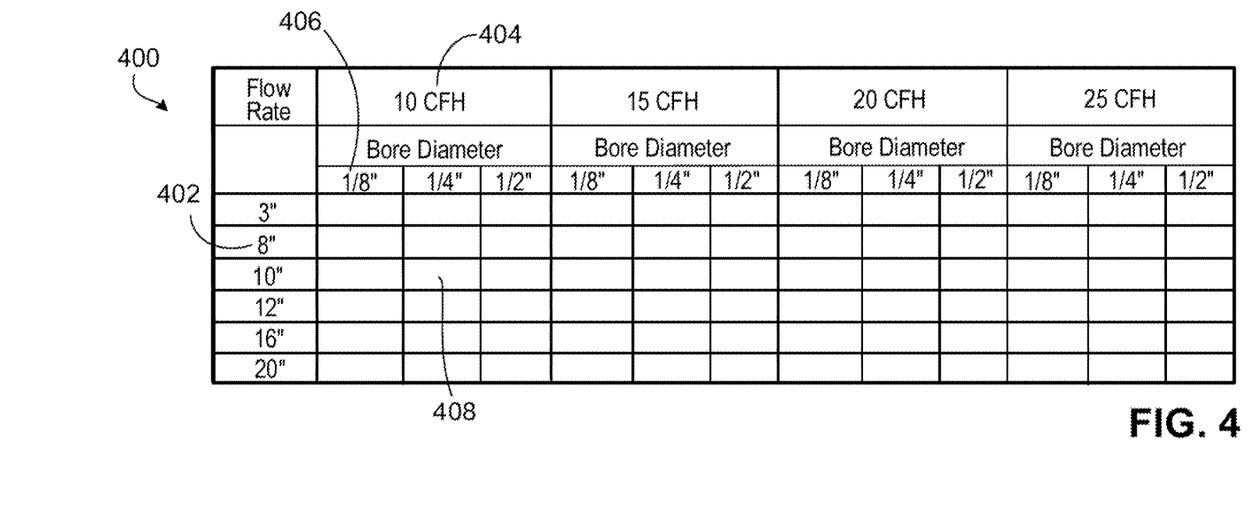
FIG. 4 is a diagram of a table for tabulating results of purge testing for welding.

FIG. 4 is an exemplary table 400 for tabulating results of purge time testing for welding piping. As indicated by the multiple data cells of the table 400, multiple tests may be performed. Moreover, an engineer or welder may utilize a completed or partially-completed table 400 to determine or specify an actual purge time, as well as purge-gas flow rate, vent size, etc., for the welding of piping in the field or shop. The table 402 gives several rows for a range of nominal diameters 402 for the test pipe (and thus for the piping to be welded). The example nominal diameters 402 listed in this table 400 are 3", 8", 10", 12", 16", and 20". Of course, other values for nominal diameter 402 can be considered, studied, and tabulated.

In this example, the flow rate 404 of the purge gas is given as a volumetric flow rate and, in particular, in cubic feet per hour (CFH) which may be standard CFH (SCFH) or actual CFH (ACFH). Other units for volumetric flow rate may be employed. Also, other types or bases of flow rates, such as mass or mass flow rate, for the purge gas may be implemented or tabulated. The illustrated example of table 400 gives four flow rates 404 along the top row of the table 400: 10 CFH, 15 CFH, 20 CFH, and 25 CFH.

For each given flow rate 404 of the purge gas, three bore sizes 406 of ⅛", ¼", and ½" are listed. These bore sizes 406 may for a pipe end enclosure disposed on the outlet or discharge end of the test pipe. This bore may be labeled or characterized as the outlet bore or vent bore.

The measured time period 408 for each test may be entered into table fields or cells associated with a corresponding test pipe diameter 402, vent bore size 406, and flow rate 404. In the illustrated example, there are 72 cells for entries of time periods 408 corresponding to tests, respectively. In application with a completed or partially-completed table 400, the shortest time period 408 for a given diameter 402 may provide a basis for actual purge time (including pre-welding preparation) for welding piping with that diameter.

Figure 5:
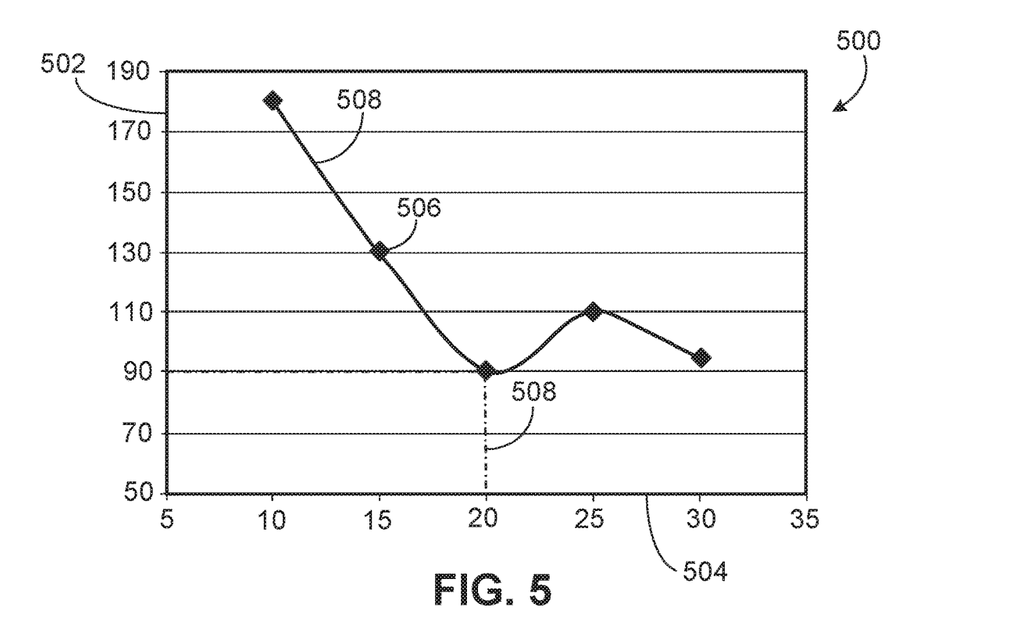
FIG. 5 is a plot of purge time versus purge flow rate in purge testing.

FIG. 5 is an example plot 500 of period of time 502 in seconds versus flow rate 504 in CFH of purge gas (e.g., argon) through a test pipe having a diameter and a vent bore size. This plot 500 are of results in purge testing. The period of time 502, which may be labeled as the test purge time, is the cumulative time or time period for the concentration of an undesired gas component (e.g., oxygen) in the purge gas flowing through the test pipe to drop to a lower threshold. The threshold may be a volume percent of 1.5, 0.5, 0.1, 0.05, or other values. The concentration may be measured, for example, at the discharge of the test pipe with a handheld gas analyzer.

Each square 506 in the plot 500 represents a purging test or purge-time test at a given flow rate 504 of purge gas through the test pipe, and the corresponding period of time 502 for the undesirable gas component in the purge gas to reach the lower threshold. Five squares 506 are plotted and a curve 508 fitted through the squares 506.

In the plot 500 for the five tests plotted, the shortest period of time 502 is 90 seconds which is at a flow rate 504 of 20 CFH, as noted by dashed line 508. The period of time 502 (test purge time) of 90 seconds and the flow rate 504 of 20 CFH may be a basis for purging piping having the same diameter to be welded. It should be noted, as indicated by the plot 500, that a higher flow rate 502 of the purge gas through the test pipe may always not lead to a shorter test purge time 502. Such may be due to turbulence or lack of steady state conditions, and so forth.

In some examples of welding stainless steel piping, the welding is not commenced until the oxygen content in the purge gas through the piping drops to a low concentration such as 0.05 vol. % or 0.05 mass % (500 ppm). The time to reach the concentration (e.g., 500 ppm O2) is determined and implemented prior to start of the welding. The flow rate of purging, or a reduced flow rate of purging, may be maintained through the welding, for example, for at least three passes or 10 mm weld metal thickness, whichever is a greater time. Such may promote that external heat source does not generate oxidation in the internal root side (root pass). The root pass may be the first weld bead deposited in a multiple pass weld, and may also be known as root sealer bead.

Figure 6:
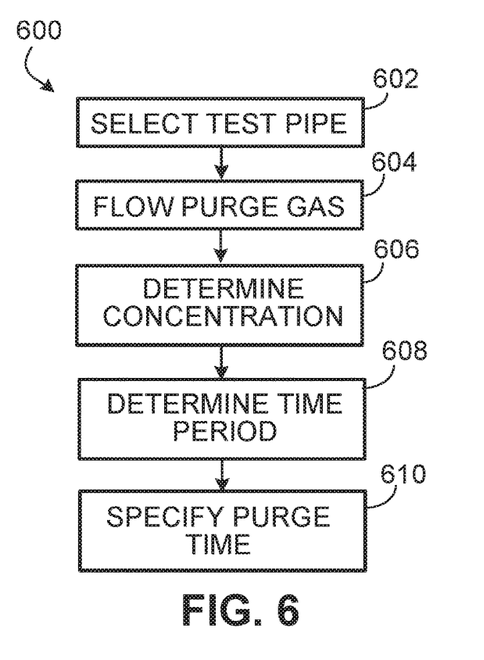
FIG. 6 is a block flow diagram of a method of performing purge-time testing for welding piping.

FIG. 6 is a method 600 of purge testing for welding piping. The method includes selecting (block 602) a test pipe from a plurality of test pipes having a range of diameters, wherein the test pipe selected has the same diameter as piping to be welded. In some embodiments, the test pipe has a length in a range of 0.5 meter to 6 meters. The test pipe may be plastic, polymer, or metal, and so on.

In certain embodiments, the method 600 includes selecting a pipe end closure having a desired bore size from a plurality of pipe end closures. The plurality of pipe end closures includes a range of bore sizes. The pipe end closure may be installed on an inlet end of the test pipe and another pipe end closure having the specified bore size installed on an outlet end of the test pipe.

The method includes flowing (block 604) purge gas (e.g., argon) at a specified flow rate through the test pipe to decrease presence of a gas component (e.g., oxygen) in the test pipe. The method 600 may include controlling flow rate of the purge gas via a flow valve of a gas cylinder to give the specified flow rate. In those embodiments employing a gas cylinder, flowing the purge gas may include flowing the purge gas from the gas cylinder through the flow valve, the pipe end enclosure, and the other pipe end closure.

Further, the method includes determining (block 606) concentration of the gas component in the purge gas discharged from the test pipe, and determining (block 608) a time period of the flowing of the purge gas through the test pipe to reach a lower threshold (e.g., 1.5 vol. % or less) of the concentration. In addition, the method includes specifying (block 610) actual purge time for welding the piping having the same diameter as the test pipe. The specified purge time may be based on (correlated with) the shortest time period determined in multiple performances of the testing with the test pipe having the same diameter as the piping to be welded. Also specified may be purge-gas flow rate, vent bore size, etc. The specified parameters including purge time may be correlative with the shortest time period and the test having the shortest time period.

In some examples, the specified flow rate includes a first specified flow rate for a first test and a second specified flow rate for a second test, wherein the time period is a first time period for the first test to reach the lower threshold and a second time period for the second test to reach the lower threshold. Indeed, the specified flow rate may include multiple specified flow rates for multiple respective tests, and wherein the time period is multiple respective time periods to reach the lower concentration threshold for each test. Again, the method 600 may include specifying (block 610) the purge time for the welding of the piping correlative with a smallest or shortest time period of the multiple time periods recorded.

Lastly, the method 600 may include selecting a second test pipe having the same diameter from the plurality of test pipes, the second test pipe longer than the test pipe. If such a selection is made, the method includes flowing a purge gas at the specified flow rate through the second test pipe and determining concentration of the gas component in the purge gas discharged from the second test pipe. The time period to reach the lower threshold of the concentration of the purge gas discharging from the second test pipe is determined to validate the time period recorder with the shorter test pipe. For example, the test pipe in the first instance may be 1 meter or 1.5 meters, and the second test pipe may be 3 meters or 4 meters.

Figure 7:
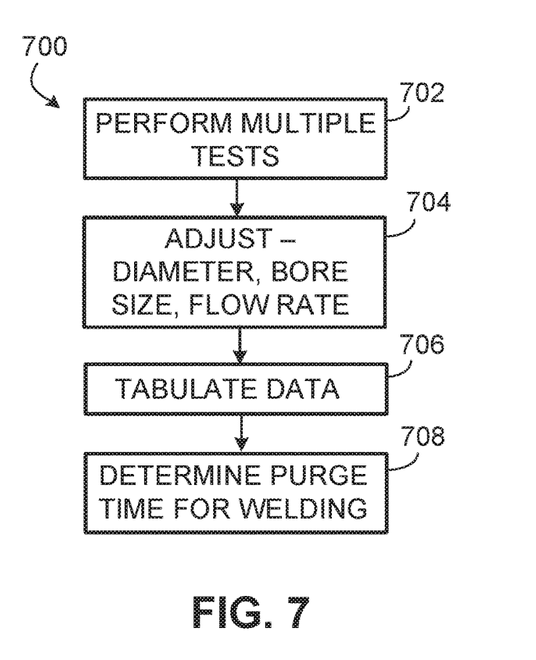
FIG. 7 is a block flow diagram of a method of determining purge time for welding piping.

FIG. 7 is a method 700 of purge-time testing for welding alloy piping such as stainless steel piping. The method includes performing (block 702) multiple purge-time tests including measuring concentration of a gas component (e.g., oxygen) in the purge gas discharged from a test pipe, and measuring a time period for the concentration to drop to a threshold concentration such as 1 vol. % or lower.

The series of tests include at least a first variable which is test pipe diameter, a second variable which is pipe-end closure bore size (vent size), and a third variable that is flow rate of purge gas through the test pipe. In examples, these three variables are independent variables. The method of performing the multiple purge-time tests includes changing or adjusting (block 704) these at least these three variables of the test-pipe diameter, the bore-size (vent size), and the flow rate of the purge gas through the test pipe.

The adjusting of the first variable (test-pipe diameter) may be to select a test pipe having a desired or specified diameter. The adjusting of the second variable (bore size) may include selecting two end closures each have a desired bore diameter and installing the two end closures on respective ends of the test pipe. Different bore sizes of the pipe end closures may be selected for different tests of the multiple tests. The adjusting of the third variable (purge-gas flow rate) may include adjusting a set point of a control valve that regulates flow of the purge gas (e.g., argon) to the test pipe. For example, a flow regulator on a gas cylinder may be adjusted to give a different flow rate of purge gas from the gas cylinder.

The determination of the actual purge time (pre-weld) for welding alloy piping having the specified diameter may be correlative with a shortest time period of the multiple-purge time tests for that specified diameter of the test pipe. Lastly, the method 700 may include performing an additional purge-time test with another test pipe having the specified diameter and that is longer (than the initial test pipe) to validate the time period. For example, the shorter (initial) test pipe may be 1 meter and the longer test pipe may be at least 3 meters to validate the test with the shorter test pipe.

In summary, an embodiment of the present techniques includes a system for testing purge time for welding piping, the system including a test pipe having a same diameter of piping to be welded. In addition, the system includes a plurality of pipe end closures to fit on an inlet end of the test pipe and on an outlet end of the test pipe, each pipe end enclosure having a bore, and the plurality having a range of bore sizes. An inlet conduit (e.g., tubing, pipe, etc.) may fluidically couple a purge-gas source (e.g. gas cylinder) to an inlet bore of an inlet pipe-end enclosure disposed on an inlet end of the test pipe, wherein the gas source discharges purge gas (e.g., argon) through the inlet conduit and the test pipe.

Further, the system includes a gas analyzer (e.g., handheld O2 analyzer) to measure a concentration of a gas component (e.g., O2) in the purge gas discharged from the test pipe. The purge gas may discharge through a vent bore or outlet bore of an outlet pipe-end enclosure disposed on an outlet end of the test pipe. In addition, the system includes a flow regulator (e.g., of the gas cylinder) to control a flow rate of the purge gas. The system may also include a timing device (e.g., clock or stopwatch) to measure a cumulative time of the flow of the purge gas through the test pipe.

In one example, an outlet conduit may couple to the outlet (vent) bore and receive the purge gas discharged from the test pipe. In that example, the gas analyzer may have a sensor disposed on the outlet conduit to measure the concentration of the gas component in the purge gas in the outlet conduit.

The system may include multiple test pipes. For instance, a first test pipe may be employed as the test pipe for a first set of tests for first piping to be welded, and a second test pipe to be employed as the test pipe for a second set of tests for second piping to be welded. The first piping and the first test pipe have a first diameter, and the second piping and the second test pipe having a second diameter different than the first diameter. Further, the plurality of pipe end enclosures may include a first plurality of pipe-end closures having the first diameter to fit on ends of the first test pipe, and a second plurality of pipe-end closures having the second diameter to fit on ends of the second test pipe. In some embodiments, the first test pipe and the second test pipe each have a length in a range of 0.5 meter to 10 meters.

Lastly, test pipes may include a first test pipe for a first test and a second test pipe for a second test to validate the first test, the second test pipe longer than the first test pipe. The first pipe and the second pipe have the same diameter. In examples, the first test pipe has a length in a range of 0.5 meter to 2 meters, such as 1 meter or 1.5 meters, and the second pipe has a length in a range of 2.5 meters to 10 meters, such as 3 meters, 4 meters, 5 meters, 6 meters, and so on.

Another embodiment includes a method of testing purge time for welding piping, including adjusting flow rate of purge gas through a test pipe for multiple tests of purge time. The method includes changing vent size for the purge gas from the test pipe for the multiple tests. The method also includes measuring concentration of a gas component of the purge gas vented from the test pipe for the multiple tests. Further, the method includes measuring a time period to drop to a lower threshold of the concentration for each test of the multiple tests. The purge gas may include argon, nitrogen, hydrogen, or helium, or any combinations thereof. The gas component may include oxygen, nitrogen, or air, or any combinations thereof. In some examples, the test pipe has a length in a range of 0.5 meter to 6 meters. The method may include specifying for welding the purge-gas flow rate, vent size, and purge time for purging of piping to be welded correlative with the test having a shortest time period of the multiple tests, and with the piping having the same nominal diameter as the test pipe. Furthermore, the method may include replacing the test pipe with a second test pipe that is longer than the test pipe, and reproducing conditions of the test having the shortest time period of the multiple tests to validate that test.

The method may also include replacing the test pipe with a second test pipe having a different nominal diameter than the test pipe, and adjusting flow rate of purge gas through the second test pipe for additional multiple tests of purge time. The method can include changing vent size for the purge gas from the second test pipe for the additional multiple tests. The method can include measuring concentration of a gas component of the purge gas vented from the second test pipe for the additional multiple tests, and measuring a time period to drop to a lower threshold of the concentration for each additional test of the additional multiple tests. Lastly, the method may include specifying for welding, the vent size, purge time, and flow rate of purge gas for purging of second piping to be welded correlative with the additional test having a shortest time period of the additional multiple tests, the second piping having a same diameter as the second test pipe.

EXAMPLE

This hypothetical example is only an example and not meant to limit the present techniques. The example employs a purging test system to determine purge conditions (including purge time) for stainless steel piping to be welded. The example stainless-steel piping to be welded has a nominal diameter of 6 inches and a length of 25 meters. The test actions in this example include the following.

1. Select a test pipe having a nominal diameter of 6 inches from a plurality of test pipes having a range of nominal diameters. The test pipe selected has a length of 1 meter.

2. Install pipe-end closures (having a bore size) on each end of the test pipe, one for an inlet and the other for an outlet (vent), and couple (with ½" tubing) an argon gas cylinder to the inlet.

3. Adjust set point of a flow regulator on the gas cylinder to give four set points of flow rates of the argon: 10 SCFH, 15 SCFH, 20 SCFH, and 25 SCFH. Stop the flow (if needed) immediately prior to each of the four set-point adjustments so that ambient air enters the test pipe.

4. For each flow rate, flow the argon from the gas cylinder as a purge gas through the ½" tubing and the test pipe, and measure the oxygen concentration with a handheld gas analyzer in the argon purge gas discharged from the outlet vent.

5. For each flow rate, measure with a stopwatch the amount of time for the oxygen concentration (measured with the gas analyzer) to drop to 0.05 vol. %. Record this amount of time for each flow rate.

6. Iterate through different bore sizes for pipe end closures. In other words, repeat actions 2, 3, 4, and 5 for different bore sizes. In this example in particular, perform actions 2, 3, 4, and 5 for three different bore sizes of ⅛", ¼", and ½". Action 5 above includes these iterations described in this action 6.

7. Select the shortest amount of time recorded in action 5. This is labeled as the shortest test purge time. In this example, the shortest amount of time as recorded in action 5 is 90 seconds which occurred at test conditions of an argon flow rate of 20 SCFH and outlet vent bore size of ¼".

8. Employ the equation below to specify an actual purge time (pre-welding) for the actual stainless-steel piping (having the length of 25 feet) to be welded.

$$\text{Actual Purge Time} = \text{Test Purge Time} \times (\text{Actual Pipe Length}/\text{Test Pipe Length}) \times \text{Factor.}$$

$$\text{Actual Purge Time} = 90 \text{ seconds} \times 25 \text{ m}/1 \text{ m} \times 1.2 = 2700 \text{ seconds (or 45 minutes).}$$

The "Factor" (=1.2 in this example) in the above equation is a contingency (dimensionless value) to promote that the purge gas for the actual welding will drop to the 0.05 vol. % oxygen prior to commencement of welding.

9. Specify actual purging conditions for this 6"-diameter stainless steel piping to be welded: purge time=45 minutes; purge-gas flow rate=20 SCFH; vent bore size=¼".

In summary, an embodiment includes a system for purge testing for welding piping. The system includes a test pipe having a same diameter of the piping to be welded, and a plurality of pipe end closures to fit on an inlet end of the test pipe and on an outlet end of the test pipe, each pipe end enclosure having a bore, wherein the plurality has a range of bore sizes. In examples, the test pipe has a length in a range of 0.5 meter to 10 meters. The system includes an inlet conduit to fluidically couple a gas source to an inlet bore of an inlet pipe-end enclosure disposed on an inlet end of the test pipe, wherein the gas source to discharge purge gas through the inlet conduit and the test pipe. The system includes a flow regulator to control flow rate of the purge gas. In some examples, the gas source is a gas cylinder having the purge gas, wherein the gas cylinder has the flow regulator with a flow gauge. The purge gas may be at least one of argon, nitrogen, or hydrogen, wherein the gas component is oxygen. Further, the system includes a gas analyzer (for example, handheld analyzer) to measure a concentration of a gas component (for example, oxygen, nitrogen, or air, or any combinations thereof) in the purge gas discharged from the test pipe through an outlet bore of an outlet pipe-end enclosure disposed on an outlet end of the test pipe. In addition, the system has a timing device (for example, clock or a stopwatch) to measure a cumulative time of the flow of the purge gas through the test pipe.

The system may include a first test pipe to be employed as the test pipe for a first set of tests for first piping to be welded, and a second test pipe to be employed as the test pipe for a second set of tests for second piping to be welded. The first piping and the first test pipe have a first diameter, and the second piping and the second test pipe have a second diameter different than the first diameter. The plurality of pipe end enclosures may include a first plurality of pipe-end closures having the first diameter to fit on ends of the first test pipe, and a second plurality of pipe-end closures having the second diameter to fit on ends of the second test pipe. In certain examples, the first test pipe and the second test pipe each have a length in a range of 0.5 meter to 10 meters.

The test pipe may be test pipes including a first test pipe for a first test and a second test pipe for a second test to validate the first test, the second test pipe longer than the first test pipe, and wherein the first test pipe and the second test pipe have the same diameter. In particular examples, the first test pipe has a length in a range of 0.5 meter to 2 meters and the second pipe has a length in a range of 2.5 meters to 10 meters.

Another embodiment is a method of purge testing for welding piping. The method incudes selecting a test pipe from a plurality of test pipes having a range of diameters, wherein the test pipe selected has a same diameter as piping to be welded. The method includes flowing a purge gas at a specified flow rate through the test pipe to decrease presence of a gas component in the test pipe. Further, the method includes determining concentration of the gas component in the purge gas discharged from the test pipe. In addition, the method includes determining a time period of the flowing of the purge gas through the test pipe to reach a lower threshold of the concentration. The specified flow rate may be a first specified flow rate for a first test and a second specified flow rate for a second test, wherein the time period is time periods including a first time period for the first test to reach the lower threshold and a second time period for the second test to reach the lower threshold. The specified flow rate may be multiple specified flow rates for multiple respective tests, and wherein the time period includes multiple respective time periods to reach the lower threshold. The method may include specifying the purge time for the welding of the piping correlative with a smallest time period of the multiple respective time periods. In one example, the purge gas includes argon, the gas component is oxygen, and the lower threshold is 1.5 volume percent or less. In some implementations, the test pipe has a length in a range of 0.5 meter to 6 meters, and wherein determining the time period includes measuring the time period with a clock or stopwatch. The method may include selecting a pipe end closure having a desired bore size from a plurality of pipe end closures having a range of bore sizes, installing the pipe end closure on an inlet end of the test pipe, and installing another pipe end closure having the specified bore size on an outlet end of the test pipe. The method may include controlling flow rate of the purge gas via a flow valve of a gas cylinder to give the specified flow rate, wherein flowing the purge gas include flowing the purge gas from the gas cylinder through the flow valve, the pipe end enclosure, and the another pipe end closure. In an implementation, the method includes selecting a second test pipe having the same diameter from the plurality of test pipes, the second test pipe longer than the test pipe. In that implementation, the method includes flowing a purge gas at the specified flow rate through the second test pipe and determining concentration of the gas component in the purge gas discharged from the second test pipe, and determining a second time period to reach the lower threshold of the concentration of the purge gas discharging from the second test pipe to validate the first time period.

Yet another embodiment is a method of purge-time testing for welding alloy piping. The method includes performing multiple purge-time tests. Test variables include a first variable that is diameter of a test pipe, a second variable that is bore size of pipe end closures installed on each end of the test pipe, and a third variable that is flow rate of a purge gas through the test pipe and the pipe end closures. In examples, the first variable, the second variable, and the third variable are independent variables. Performing each test of the multiple purge-time tests further includes measuring concentration of a gas component in the purge gas discharged from the test pipe, and measuring a time period for the concentration to drop to a threshold concentration. Further, performing the multiple purge-time tests may include adjusting the first variable, the second variable, and the third variable, wherein adjusting the first variable includes selecting a test pipe comprising a specified diameter, wherein adjusting the second variable includes selecting two end closures each comprising a desired bore diameter and installing the two end closures on respective ends of the test pipe, and wherein adjusting the third variable includes adjusting a set point of a control valve that regulates flow of the purge gas to the test pipe. In examples, the alloy piping is stainless steel piping, wherein the purge gas comprises argon, wherein the gas component is oxygen, and wherein the threshold concentration is 0.1 volume percent (%) or less. The method may include determining a purge time for welding alloy piping having the specified diameter correlative with a shortest time period for that specified diameter of the test pipe of the multiple-purge time tests. The method may include performing an additional purge-time test with another test pipe comprising the specified diameter and that is longer than the test pipe to validate the time period.

Yet another embodiment is a method of performing multiple tests to determine purge time for welding piping. The method includes flowing a purge gas at a respective flow rate through a test pipe for each test, the test pipe comprising a same diameter as the piping to be welded. The method includes determining a concentration of a gas component in the purge gas discharged from the test pipe for each test. Further, the method includes determining a respective time period to reach a lower threshold of the concentration for each test. The method also includes specifying a purge time for the welding of the piping correlative with a shortest time period of the respective time periods.

A number of implementations have been described. Nevertheless, it will be understood that various modifications may be made without departing from the spirit and scope of the disclosure.

What is claimed is:

1. A system for purge testing to determine pre-welding purge time for piping to be welded, the system comprising:
   a test pipe comprising a same diameter of the piping to be welded;
   a plurality of pipe end closures to fit on an inlet end of the test pipe and on an outlet end of the test pipe, each pipe end enclosure comprising a bore, wherein the plurality of pipe end closures comprises a range of bore sizes;
   an inlet conduit to fluidically couple a gas source to an inlet bore of an inlet pipe-end enclosure disposed on an inlet end of the test pipe, wherein the gas source to discharge purge gas through the inlet conduit and the test pipe;
   a gas analyzer to measure a concentration of a gas component in the purge gas discharged from the test pipe through an outlet bore of an outlet pipe-end enclosure disposed on an outlet end of the test pipe;
   a flow regulator to control a flow rate of the purge gas;
   a timing device to measure a cumulative time of the flow of the purge gas through the test pipe; and
   a validation test pipe that is at least three times longer than the test pipe to perform a validation test to validate a test performed with the test pipe, wherein the validation test pipe and the test pipe comprise a same diameter.

2. The system of claim 1, comprising:
   a first test pipe in the system for purge testing to be employed as the test pipe for a first set of tests for first piping to be welded; and
   a second test pipe in the system for purge testing to be employed as the test pipe for a second set of tests for second piping to be welded, the first piping and the first test pipe comprising a first diameter, and the second piping and the second test pipe comprising a second diameter different than the first diameter.

3. The system of claim 2, wherein the plurality of pipe end enclosures comprises a first plurality of pipe-end closures comprising the first diameter to fit on ends of the first test pipe, and a second plurality of pipe-end closures comprising the second diameter to fit on ends of the second test pipe.

4. The system of claim 2, wherein the first test pipe and the second test pipe each comprise a length in a range of 0.5 meter to 10 meters, wherein the gas component comprises oxygen, nitrogen, or air, or any combinations thereof, and wherein the gas analyzer comprises a handheld analyzer.

5. The system of claim 1, wherein the test pipe is not the piping to be welded, wherein the purge gas comprises at least one of argon, nitrogen, or hydrogen, wherein the gas component comprises oxygen, and wherein the timing device comprises a clock or a stopwatch.

6. The system of claim 1, comprising the gas source comprising a gas cylinder having the purge gas, wherein the gas cylinder comprises the flow regulator comprising a flow gauge, wherein the test pipe is non-metallic, and wherein the test pipe comprises a length in a range of 0.5 meter to 10 meters.

7. The system of claim 1, wherein the test pipe is a single piece of pipe that is a test spool piece, and wherein the piping to be welded comprises two pieces of pipe.

8. The system of claim 1, wherein the piping to be welded is longer than the test pipe, wherein the test pipe comprises a length in a range of 0.5 meter to 2 meters and the validation test pipe comprises a length in a range of 2.5 meters to 10 meters.

9. A method of purge testing with test piping to determine pre-welding purge time for piping to be welded, comprising:
   selecting a test pipe from a plurality of test pipes comprising a range of diameters, wherein the test pipe selected comprises a same diameter as the piping to be welded;
   flowing a purge gas at a specified flow rate through the test pipe to decrease concentration of a gas component in the test pipe;
   determining the concentration of the gas component in the purge gas discharged from the test pipe;
   determining a time period of the flowing of the purge gas through the test pipe to reach a lower threshold of the concentration, wherein the specified flow rate comprises multiple specified flow rates for multiple respective tests, and wherein the time period comprises multiple respective time periods to reach the lower threshold for the multiple respective tests; and
   specifying the pre-welding purge time for the piping to be welded correlative with a smallest time period of the multiple respective time periods.

10. The method of claim 9, wherein the piping to be welded is longer than the test pipe, wherein the purge gas comprises argon, the gas component comprises oxygen, and the lower threshold comprises 1.5 volume percent or less, wherein the test pipe comprises a length in a range of 0.5 meter to 6 meters, and wherein determining the time period comprises measuring the time period with a clock or stopwatch.

11. The method of claim 9, comprising:
   selecting a pipe end closure having a desired bore size from a plurality of pipe end closures comprising a range of bore sizes;
   installing the pipe end closure on an inlet end of the test pipe; and
   installing another pipe end closure having the specified bore size on an outlet end of the test pipe.

12. The method of claim 11, comprising controlling flow rate of the purge gas via a flow valve of a gas cylinder to give the specified flow rate, wherein flowing the purge gas comprises flowing the purge gas from the gas cylinder through the flow valve, the pipe end enclosure, and the another pipe end closure, and wherein the test pipe is non-metallic.

13. The method of claim 9, wherein the multiple specified flow rates comprise a first specified flow rate for a first test and a second specified flow rate for a second test, wherein the multiple respective time periods comprise a first time period for the first test to reach the lower threshold and a second time period for the second test to reach the lower threshold, and wherein the test pipe is not the piping to be welded.

14. The method of claim 9, comprising:
specifying a purge-gas flow rate for purging the piping to be welded, wherein the purge-gas flow rate is the flow rate of the multiple specified flow rates that gave the smallest time period; and
purging the piping to be welded with the purge gas at the purge-gas flow rate for the pre-welding purge time as specified.

15. The method of claim 14, comprising welding the piping after purging the piping for the pre-welding purge time as specified.

16. The method of claim 9, comprising:
selecting a second test pipe comprising the same diameter from the plurality of test pipes, the second test pipe at least three times longer than the test pipe;
flowing a purge gas at the specified flow rate through the second test pipe and determining concentration of the gas component in the purge gas discharged from the second test pipe; and
determining a second time period to reach the lower threshold of the concentration of the purge gas discharging from the second test pipe to validate the first time period.

17. A method of purge-time testing to determine pre-welding purge time for welding alloy piping, comprising:
performing multiple purge-time tests comprising adjusting a first variable comprising diameter of a test pipe, a second variable comprising bore size of pipe end closures installed on each end of the test pipe, and a third variable comprising flow rate of a purge gas through the test pipe and the pipe end closures, wherein performing each test of the multiple purge-time tests further comprises:
measuring concentration of a gas component in the purge gas discharged from the test pipe; and
measuring a time period for the concentration to drop to a threshold concentration; and
determining a pre-welding purge time for welding alloy piping correlative with a shortest time period in the multiple-purge time tests for the concentration to drop to a threshold concentration with the diameter of the test pipe comprising a diameter of the alloy piping.

18. The method of claim 17, comprising:
specifying a purge-gas flow rate that is the flow rate of the purge gas for the shortest time period; and
purging the alloy piping at the purge-gas flow rate for the pre-welding purge time before welding the alloy piping.

19. The method of claim 17, wherein adjusting the first variable comprises selecting a test pipe comprising a specified diameter, wherein adjusting the second variable comprises selecting two end closures each comprising a desired bore diameter and installing the two end closures on respective ends of the test pipe, and wherein adjusting the third variable comprises adjusting a set point of a control valve that regulates flow of the purge gas to the test pipe.

20. The method of claim 18, wherein determining the pre-welding purge time comprises determining the pre-welding purge time for welding alloy piping having the specified diameter correlative with the shortest time period for that specified diameter of the test pipe of the multiple-purge time tests as the diameter of the test pipe comprising a diameter of the alloy piping.

21. The method of claim 20, comprising performing an additional purge-time test with another test pipe comprising the specified diameter and that is longer than the test pipe to validate the shortest time period.

22. The method of claim 17, wherein the first variable, the second variable, and the third variable are independent variables, wherein the alloy piping comprises stainless steel piping, wherein the purge gas comprises argon, wherein the gas component comprises oxygen, and wherein the threshold concentration is 0.1 volume percent (%) or less.

23. A method of performing multiple tests with test piping to determine pre-welding purge time for piping to be welded, comprising:
flowing a purge gas at a respective flow rate through a test pipe for each test of the multiple tests, the test pipe comprising a same diameter as the piping to be welded, wherein the test pipe is shorter in length than the piping to be welded;
determining a concentration of a gas component in the purge gas discharged from the test pipe for each test;
determining a respective time period to reach a lower threshold of the concentration for each test; and
specifying a pre-welding purge time and purge-gas flow rate for the welding of the piping to be welded correlative with a shortest time period of the respective time periods.

24. The method of claim 23, comprising purging the piping to be welded with the purge gas at the purge-gas flow rate for the pre-welding purge time before welding the piping, wherein the piping comprises two pieces of pipe, wherein the purge gas comprises at least one of argon, nitrogen, or hydrogen, wherein the gas component comprises oxygen, wherein the lower threshold comprises 1.5 volume percent or less, and wherein the test pipe comprises a length in a range of 0.5 meter to 10 meters.

* * * * *